United States Patent [19]

de Rosset

[11] 4,213,913

[45] Jul. 22, 1980

[54] TWO-STAGE PROCESS FOR SEPARATING MIXED FATTY-ACID ESTERS

[75] Inventor: Armand J. de Rosset, Clarendon Hills, Ill.

[73] Assignee: UOP Inc., Des Plaines, Ill.

[21] Appl. No.: 19,966

[22] Filed: Mar. 12, 1979

[51] Int. Cl.$^2$ .......................... C09F 5/10; C11B 3/00
[52] U.S. Cl. ............................ 260/428.5; 260/428; 560/218; 560/248
[58] Field of Search .................. 260/428.5, 428; 560/218, 248

[56] References Cited

U.S. PATENT DOCUMENTS

| | | | |
|---|---|---|---|
| 4,006,197 | 1/1977 | Bieser | 208/310 Z |
| 4,066,677 | 1/1978 | de Rosset et al. | 260/428.5 |

*Primary Examiner*—John F. Niebling
*Attorney, Agent, or Firm*—James R. Hoatson, Jr.; Louis A. Morris; William H. Page, II

[57] ABSTRACT

A process for separating an ester of a polyethanoid fatty acid and an ester of a monoethanoid fatty acid from a mixture comprising an ester of a polyethanoid fatty acid, an ester of a monoethanoid fatty acid and an ester of a saturated fatty acid which process comprises contacting the mixture at first adsorption conditions with a first adsorbent comprising an X or a Y zeolite containing a selected cation at the exchangeable cationic sites thereby selectively adsorbing the ester of a polyethanoid fatty acid and thereafter recovering the ester of a polyethanoid fatty acid by desorption with a desorbent material; removing from the first adsorbent a second mixture comprising an ester of a monoethanoid fatty acid and an ester of a saturated fatty acid; contacting the second mixture at second adsorption conditions with a second adsorbent comprising an X or a Y zeolite containing selected cations at the exchangeable cationic sites thereby selectively adsorbing the ester of a monoethanoid fatty acid and thereafter recovering the ester of a monoethanoid fatty acid by desorption with desorbent material having the same composition as the first mentioned desorbent material. The polyethanoid fatty acid and monoethanoid fatty acid esters are separated from the desorbent material by a single separation means.

14 Claims, 1 Drawing Figure

TWO-STAGE PROCESS FOR SEPARATING MIXED FATTY-ACID ESTERS

BACKGROUND OF THE INVENTION

1. Field of the Invention

Figure 1:
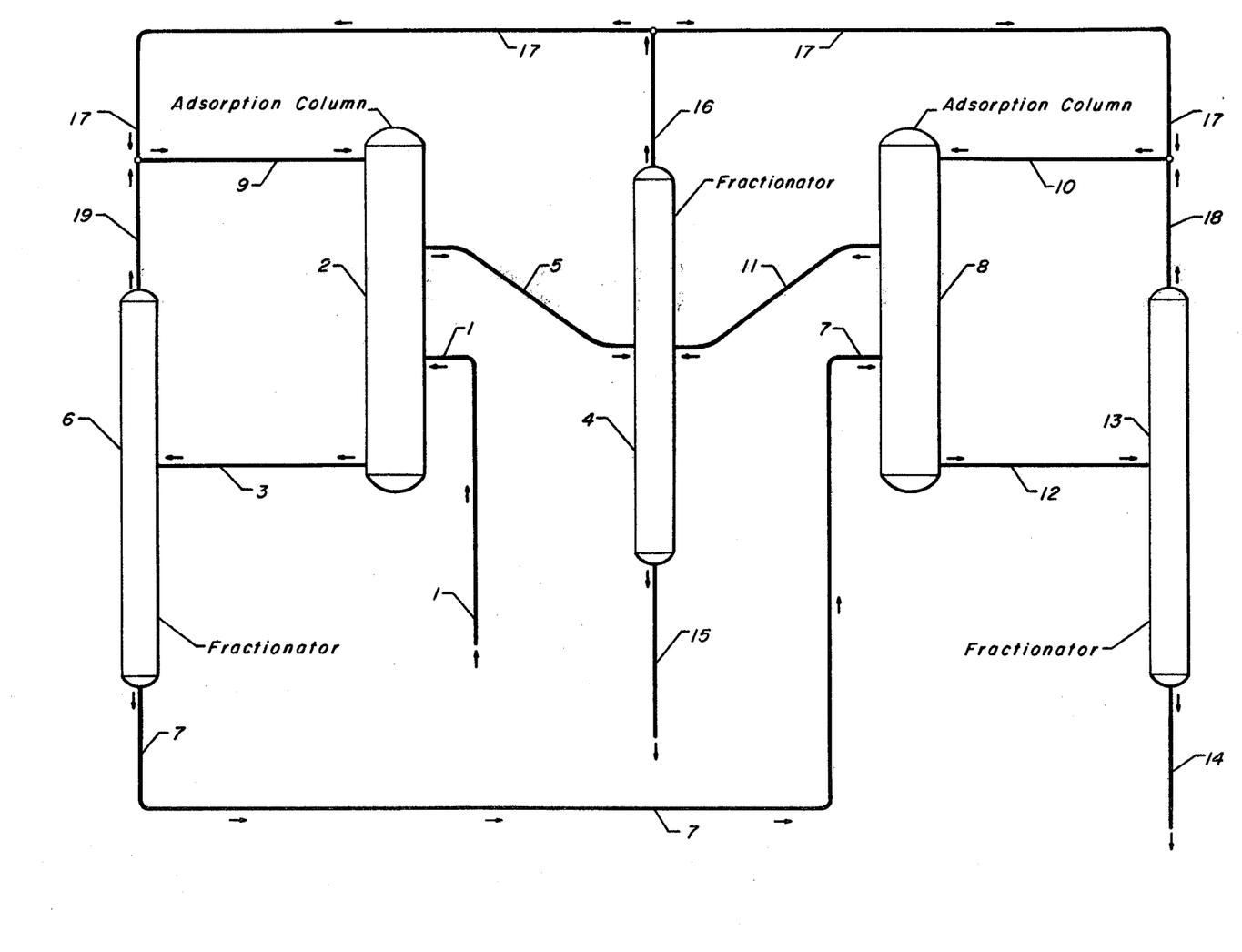

The field of art to which this invention pertains is the solid bed adsorptive separation of mixed fatty-acid esters using zeolite adsorbents. More specifically, the invention relates to a process for separating an ester of a polyethanoid fatty acid and an ester of a monoethanoid fatty acid from a mixture comprising an ester of a polyethanoid fatty acid, an ester of a monoethanoid fatty acid and an ester of a saturated fatty acid, which process employs a first zeolitic adsorbent which selectively adsorbs an ester of a polyethanoid fatty acid and a second zeolitic adsorbent which selectively adsorbs an ester of a monoethanoid fatty acid, the desorption of said esters being effected by means of the same composition desorbent material for both adsorbents with separation of said adsorbed esters from the desorbent material being effected by a single separating means.

2. Description of the Prior Art

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched-chain paraffins and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Y zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; in the process described in U.S. Pat. No. 3,668,267 to separate specific alkyl-substituted naphthalenes. Because of the commercial importance of para-xylene, perhaps the more well-known and extensively used hydrocarbon isomer separation processes are those for separating para-xylene from a mixture of $C_8$ aromatics. In processes described in U.S. Pat. Nos. 3,558,730; 3,558,732; 3,626,020; 3,663,638; and 3,734,974 for example adsorbents comprising particular zeolites are used to separate para-xylene from feed mixtures comprising para-xylene and at least one other xylene isomer by selectively adsorbing para-xylene over the other xylene isomers.

It is also known to the art, from U.S. Pat. No. 4,049,688, that adsorbents comprising an X or Y zeolite containing one or more selected cations at the exchangeable cationic sites selected from the group consisting of cations of metals of Group IA of the Periodic Table of Elements exhibit adsorptive selectivity for an ester of an unsaturated fatty acid with respect to an ester of a saturated fatty acid thereby making separation of such esters by solid-bed selective adsorption possible.

U.S. Pat. No. 4,066,677 teaches further that a first adsorbent comprising a X or a Y zeolite containing certain selected cations at the exchangeable cationic sites exhibits higher adsorptive selectivity for an ester of a polyethanoid fatty acid than for either an ester of a monoethanoid fatty acid or an ester of a saturated fatty acid and that a second adsorbent comprising an X or a Y zeolite containing certain selected cations at the exchangeable cationic sites, preferably copper and potassium cations, exhibits adsorptive selectivity for a monoethanoid fatty acid with respect to an ester of a saturated fatty acid thereby making separation of an ester of a polyethanoid fatty acid and an ester of a monoethanoid fatty acid by solid-bed selective adsorption possible.

I have discovered a process flow scheme that enables the separation of polyethanoid, monoethanoid and saturated fatty acids in a particularly efficient manner.

Production of fatty esters is the most important phase in the industrial chemistry of fatty acids. The esters produced are of several types and include those resulting from the reaction of fatty acids with monohydric alcohols, polyhydric alcohols, ethylene or propylene oxide, and acetylene or vinyl acetate. The principal monohydric alcohols are methanol, 1-propanol, 2-propanol and 1-butanol. The greatest uses of fatty-acid esters in general are in the solvent and plasticizer fields. Esters of monohydric alcohols are used for plasticizers and in cosmetics. Esters of saturated fatty acids are of value in compounding lubricating oil, as a lubricant for the textile and molding trade, in special lacquers, as a waterproofing agent, and in the cosmetic and pharmaceutical fields. Esters of unsaturated fatty acids find use as drying agents.

SUMMARY OF THE INVENTION

It is accordingly a broad objective of my invention to provide a process for separating an ester of a polyethanoid fatty acid and an ester of a monoethanoid fatty acid from a feed mixture containing an ester of a polyethanoid fatty acid, an ester of a monoethanoid fatty acid and an ester of a saturated fatty acid to produce one product stream containing a higher concentration of the esters of a polyethanoid fatty acid and monoethanoid fatty-acid relative to the saturated fatty-acid esters than was contained in the feed mixture, and a second product stream containing a higher concentration of a saturated fatty-acid ester relative to other fatty-acid esters than was contained in the feed mixture. More specifically, it is an objective of my invention to provide a flow scheme for such a process that enables its operation in a particularly efficient manner and with a minimum of equipment and associated capital investment.

In brief summary, my invention is a process for separating an ester of a polyethanoid fatty acid and an ester of a monoethanoid fatty acid from a first mixture comprising an ester of a polyethanoid fatty acid, an ester of a monoethanoid fatty acid and an ester of a saturated fatty acid which process comprises the steps of: (a) contacting said first mixture at first adsorption conditions with a first adsorbent comprising a X or a Y zeolite containing at the exchangeable cationic sites at least one cation selected from the group consisting of cations of metals of Group IA of the Periodic Table of Elements and combinations thereof thereby selectively adsorbing said ester of a polyethanoid fatty acid; (b) removing from said first adsobent a first raffinate output stream comprising said ester of a monoethanoid fatty acid and said ester of a saturated fatty acid; (c) contacting said first adsorbent at first desorption conditions with a desorbent material to effect the desorption of said ester of a polyethanoid fatty acid from said first adsorbent; (d) removing from said first adsorbent a first extract output stream comprising said ester of a polyethanoid fatty acid; (e) contacting a second mixture comprising said first raffinate output stream at second adsorption conditions with a second adsorbent comprising a X or a Y zeolite containing at exchangeable cationic sites cations selected from the group consisting of pi-bonding metals and one or more second cations selected from the group consisting of sodium, potassium, rubidium and cesium, thereby selectively adsorbing said ester of a monoethanoid fatty acid; (f) removing from said second adsorbent a second raffinate output stream comprising said ester of a saturated fatty acid; (g) contacting said second adsorbent at second desorption conditions with a desorbent material having the same composition as the desorbent material used in step (c) above to effect the desorption of said ester of a monoethanoid fatty acid from said second adsorbent; (h) removing from said second adsorbent a second extract output stream comprising said ester of a monoethanoid fatty acid; and (i) passing said first extract output stream and said second extract output stream to a single desorbent recovery means wherein substantially all of said desorbent material contained in said streams is recovered for re-use in said process, and further recovering from said desorbent recovery means an extract product stream comprising substantially all of said esters of a polyethanoid fatty acid and monoethanoid fatty acid contained in said first mixture.

Other objectives and embodiments of my invention encompass details about feed mixtures, adsorbents, desorbent materials and operating conditions all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A "feed mixture" is a mixture containing one or more extract components and one or more raffinate components to be fed to an adsorbent of our process. The term "feed stream" indicates a stream of a feed mixture which passes to an adsorbent used in the process.

An "extract component" is a compound or type of compound that is more selectively adsorbed by an adsorbent while a "raffinate component" is a compound or type of compound that is less selectively adsorbed. Considering the first adsorbent (hereinafter discussed in more detail) of this process, an ester of a polyethanoid fatty acid is an extract component and an ester of a monoethanoid fatty acid and an ester of a saturated fatty acid are both raffinate components. Considering the second adsorbent (hereinafter discussed in more detail) of this process, an ester of a monoethanoid fatty acid is an extract component and an ester of a saturated fatty acid is a raffinate component. The term "desorbent material" shall mean generally a material capable of desorbing an extract component from an adsorbent. The term "desorbent stream" or "desorbent input stream" indicates the stream through which a desorbent material passes to an adsorbent. The term "raffinate stream" or "raffinate output stream" means a stream through which a raffinate component is removed from an adsorbent. The composition of the raffinate stream can vary from essentially 100% desorbent material to essentially 100% raffinate components. In this process there is a first raffinate output stream from the first adsorbent and a second raffinate output stream from the second adsorbent. The first raffinate output stream may comprise the feed stream to the second adsorbent or alternatively, if the first raffinate output stream contains desorbent material, at least a portion of desorbent material may be removed from this raffinate output stream prior to being fed to the second adsorbent. The term "extract stream" or "extract output stream" shall mean a stream through which an extract component which has been desorbed by a desorbent material is removed from an adsorbent. The composition of an extract stream, likewise, can vary from essentially 100% desorbent material to essentially 100% extract components. In this process there is a first extract stream from the first adsorbent and a second extract stream from the second adsorbent. Although it is possible by the process of this invention to produce a high-purity extract product or a raffinate product (or both) at high recoveries, it will be appreciated that an extract component is never completely adsorbed by the adsorbent, nor is a raffinate component completely non-adsorbed by the adsorbent. Therefore, varying amounts of a raffinate component can appear in an extract stream and, likewise, varying amounts of an extract component can appear in a raffinate stream. The extract and raffinate streams then are further distinquished from each other and from the feed mixture by the ratio of the concentrations of an extract component and a raffinate component appearing in the particular stream. Considering the effluent streams from the second adsorbent for example, the ratio of the concentration of a monoethanoid fatty-acid ester to that of a less-selectively adsorbed, saturated-fatty-acid ester will be lowest in the second raffinate stream, next highest in the second feed mixture, and highest in the second extract stream. Likewise, the ratio of the concentration of a less-selectively-adsorbed, saturated-fatty-acid ester to that of a more-selectively-adsorbed, monoethanoid-fatty-acid ester will be highest in the second raffinate stream, next highest in the second feed mixture, and the lowest in the second extract stream.

When they contain desorbent materials at least a portion of an extract stream and preferably at least a portion of a raffinate stream from the separation process will be passed to separation means, typically fractionators, where at least a portion of desorbent material will be separated at separating conditions to produce an extract product and a raffinate product. The terms "extract product" and "raffinate product" mean products produced by the process containing, respectively, an extract component and a raffinate component in higher concentrations than those found in the respective extract stream and the raffinate stream.

The term "selective pore volume" of an adsorbent is defined as the volume of an adsorbent which selectively adsorbs an extract component from a feed mixture. The term "non-selective void volume" of an adsorbent is the volume of an adsorbent which does not selectively retain an extract component from a feed mixture. This volume includes the cavities of an adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When an adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the moving adsorbent to displace the fluid present in the non-selective void volume. If the fluid flow rate passing into a zone smaller than the non-selective void volume rate of an adsorbent material passing into that zone there, is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb a raffinate component from the fluid surrounding the adsorbent since in certain instances there is competition between an extract component and a raffinate component for adsorptive sites within the selective pore volume. If a large quantity of raffinate component with respect to an extract component surrounds an adsorbent, a raffinate component can be competitive enough to be adsorbed by an adsorbent.

The term "pi-bonding metal" is defined as a metal in the group consisting of those transition elements in the Periodic Table of Elements which form mono-olefin pi-complexes. The term "pi-complex" refers to a type of configuration or inter-relationship of the orbital electrons of the atoms of the metal and certain atoms of the olefin in the complex. The known pi-bonding metals are vanadium, and the metals of Groups VIB, VII, VIII and IB of the Periodic Table of Elements.

Before considering feed mixtures which can be charged to the process of my invention, brief reference is first made to the terminology and to the general production of fatty acids used to make the fatty-acid esters. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched-chain, it is now generally used, and is so used herein, to include also related unsaturated acids, certain substituted acids, and even aliphatic acids containing alicyclic substituents. The naturally-occurring fatty acis with a few exceptions are higher straight-chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). Thus the term "unsaturated fatty acid" is a generic term for a fatty acid having at least one double bond. The term "monoethanoid fatty acid" means a fatty acid having one double bond per molecule and the term "polyethanoid fatty acid" means a fatty acid having more than one double bond per molecule. Fatty acids are typically prepared from glyceride fats or oils by one of several "splitting" or hydrolytic processes. In all cases the hydrolysis reaction may be summarized as the reaction of a fat or oil with water to yield fatty acids plus glycerol. In modern fatty acid plants this process is carried out by continuous high-pressure, high-temperature hydrolysis of the fat. Starting materials most commonly used for the production of fatty acids include coconut oil, palm oil, inedible animal fats, and the commonly-used vegetable oils, soybean oil, cottonseed oil and corn oil. The composition of the fatty acids obtained from the "splitter" is dependent on the fat or oil from which they were made. As detailed data for the fatty-acid composition of fats have accumulated over a wide range of material it has become more and more apparent that natural fats tend to align themselves, by their component acids, in groups according to their biological origin. Moreover, it has become clear that the fats of the simplest and most primitive organisms are usually made up from a very complex mixture of fatty acids whereas as biological development has proceeded, the chief component acids of the fats of the higher oganisms have become fewer in number. In the animal kingdom this change in type is remarkably consistent and culminates in the fats of the higher land mammals, in fats in which oleic, plamitic and stearic acids are the only major components. All fats of aquatic origin contain a wide range of combined fatty acids, mainly of the unsaturated series. On passing from fats of aquatic to those of land animals there is also a marked simplification in the composition of the mixed fatty acids; most of the unsaturated acids, except oleic acid, disappear. The final result is that in most of the higher land animals the major component acids of the fats are restricted to oleic, palmitic and stearic and, moreover, that about 60–65% of the acids belong to the $C_{18}$ series, saturated or unsaturated. Thus the composition of the fatty acids obtained from the splitter can vary widely depending upon the fat or oil charged to the splitter. Rarely will the composition of the fatty acid mixture obtained from the "splitter" be ideal or even satisfactory for most uses. Hence fractionation is used almost universally to prepare fatty-acid products more desirable for specific end uses than the fatty-acid mixtures obtained from the "splitter". Fractionation according to molecular weight is best accomplished in fractional distillation. There is a marked difference in the volatility of any two fatty acids of different chain length, and in practice the utility of fractional distillation is enhanced by the absence of odd-membered acids in the natural fats, so that 2 carbon atoms is nearly always the minimum difference in chain length of the fatty acids present in a mixture. Fractionating columns in such operations are capable of producing fatty acids of 95% purity or better from the viewpoint of chain length. It is not possible, however, to separate unsaturated fatty acids from each other or from saturated fatty acids by commercial fractional distillation when all have the same chain length. While unsaturated fatty acids can be separated from saturated fatty acids by fractional crystallization with or without the use of solvents, typically a mixture of unsaturated and saturated fatty acids having the same carbon number chain length or having chain lengths over a narrow carbon-number range will be used rather than pure compounds to prepare the end-use products, such as fatty acid esters. When such a mixture is esterified, such as with a monohydric alcohol, a mixture of unsaturated and saturated fatty-acid esters is produced which is equally difficult if not impossible to separate by fractional distillation.

My process is directed to separating certain mixtures of these unsaturated and saturated fatty-acid esters; more specifically it is directed to separating an ester of a polyethanoid fatty acid and an ester of a monoethanoid fatty acid from mixtures comprising an ester of a polyethanoid fatty acid, an ester of a monoethanoid fatty acid and an ester of a saturated fatty acid. Feed mixtures charged to the first adsorbent used in our process will comprise an ester of a polyethanoid fatty acid, an ester of a monoethanoid fatty acid and an ester of a saturated fatty acid. The feed mixtures may contain one or more polyethanoid fatty-acid esters, one or more monoethanoid fatty-acid ester and one or more saturated fatty-acid ester. Preferably the esters in feed mixtures will each contain from about 8 to about 30 carbon atoms per molecule and will be produced by the reaction of fatty acids with monohydric alcohols. Particularly preferred are methyl and ethyl esters of such fatty acids. Typically the fatty-acid esters will either all have the same carbon number chain length or will have carbon number chain lengths that do not vary more than about 1 to about 5 carbon numbers from each other. An example of a typical feed mixture is one containing: 1 vol. % $C_{14}$ and lower saturated compounds; 25 vol. % methyl palmitate; 18 vol. % methyl stearate; 44 vol. % methyl oleate; and 11 vol. % methyl linoleate. Except for the small amount of $C_{14}$ material such feed mixture consists of $C_{16}$ and $C_{18}$ methyl esters of fatty acids and more specifically consists of two saturated fatty-acid esters, one monoethanoid fatty-acid ester and one diethanoid fatty-acid ester. Feed mixtures which can be charged to my process may contain, in addition to fatty-acid esters, a diluent material that is not adsorbed by the adsorbent and which is preferably separable from the extract and raffinate output streams by fractional distillation. Paraffinic hydrocarbons are examples of suitable diluents. Normal heptane is one specific example of a paraffinic hydrocarbon that can be used as a diluent. When a diluent is employed the concentration of diluent in the mixture of diluent and fatty-acid esters will preferably be from a few vol. % up to about 75 vol. % with the remainder being fatty-acid ester.

In my process a feed mixture comprising an ester of a polyethanoid fatty acid, a monoethanoid fatty acid and a saturated fatty acid is contacted at first desorption conditions with a first adsorbent thereby selectively adsorbing an ester of a polyethanoid fatty acid which is subsequently recovered and a first raffinate stream comprising an ester of a monoethanoid fatty acid and an ester of a saturated fatty acid is withdrawn from the first adsorbent. This first raffinate stream will then comprise the second feed mixture to be charged to the second adsorbent used in the process. If the first raffinate stream contains desorbent material, the stream may first be passed to a separation means wherein a portion or essentially all of the desorbent material will be separated from the stream prior to its being charged to the second adsorbent. The second feed mixture may contain, in addition to the first raffinate stream, a diluent of the type and in a concentration as described above. Preferably the second feed mixture charged to the second adsorbent will contain less than 1–2 vol. % and more preferably less than about 0.1–0.2 vol. % of an ester of a polyethanoid fatty acid. It is known from the art that such esters of polyethanoid fatty acids are adsorbed so strongly by the second adsorbent employed in the process that they cannot be desorbed with a desorbent material. These tightly-adsorbed esters of polyethanoid fatty acids then eventually interfere with the selective adsorption of an ester of a monoethanoid fatty acid.

Desorbent materials used in various prior art adsorptive separation processes vary depending upon such factors as the type of operation employed. In the swing-bed system in which a selctively adsorbed feed component is removed from the adsorbent by a purge stream desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, a desorbent material must be judiciously selected to satisfy many criteria. First, a desorbent material should displace an extract component from an adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that an adsorbent be more selective for all extract components with respect to a raffinate component than it is for a desorbent material with respect to a raffinate component. Secondly, desorbent materials must be compatible with a particular adsorbent and a particular feed mixture. More specifically, a desorbent material must not reduce or destroy the critical selectivity of an adsorbent for an extract component with respect to a raffinate component. A desorbent material should additionally be a substance which is easily separable from the feed mixture then is passed into the process. A raffinate stream and an extract stream removed from an adsorbent both typically contain desorbent material and without a method of separating at least a portion of the desorbent material the purity of an extract product and a raffinate product would not be very high, nor would a desorbent material be available for reuse in the process. It is therefore contemplated that any desorbent material used in this process will preferably have a substantially different average boiling point than that of a feed mixture to allow separation of at least a portion of desorbent material from feed components in an extract and a raffinate stream by simple fractional distillation thereby permitting reuse of a desorbent material in the process. The term "substantially different" as used herein shall mean that the difference between the average boiling points between a desorbent material and a feed mixture shall be at least about 5° C. The boiling range of a desorbent material may be higher or lower than that of a feed mixture. Finally, a desorbent material should also be a material which is readily available and therefore reasonable in cost. In the preferred isothermal, isobaric, liquid-phase operation of the process of my invention, desorbent materials comprising monocyclic aromatic hydrocarbons having average boiling points substantially different from that of a feed mixture meet these requirements and are particularly effective in desorbing adsorbed components from both the first and second adsorbents. Preferred monocyclic aromatic hydrocarbons are benzene, toluene, xylenes, ethylbenzene and diethylbenzenes. Usually one of these preferred desorbent materials can be employed with a particular feed mixture such that the requirement of substantially different average boiling points is met. Mixtures of a monocyclic aromatic with a diluent that is compatible with the adsorbents and feed mixtures used in my process and that is easily separable from the feed mixture are also effective as desorbent materials. Diluents meeting these requirements can be selected from straight-, branched-chain, or cycloparaffins. Typical concentrations of a monocyclic aromatic hydrocarbon in such mixtures can be from a few volume percent up to near 100 volume percent of the total desorbent material mixture but such concentrations preferably will be within the range of from about 50 vol. % to about 100 vol. % of the mixture.

It is essential in the practice of this invention that desorbent materials having the same composition are used for both the first and second adsorbents. This enables the use of a single desorbent recovery means for both extract output streams.

The prior art has also recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and a desorbent material; and sufficiently fast rates of adsorption and desorption of an extract component to and from an adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of an adsorbent be maintained during actual use in the separation process over some economically desirable life. The second necessary adsorbent characteristic is the ability of an adsorbent to separate components of the feed; or, in other words, that an adsorbent possess adsorptive selectivity, (B), for one component as compared to another component. Relative selectivity can be expressed not only for one feed component as compared to another but can also be expressed between any feed mixture component and the desorbent material. The term "selectivity", (B), as used throughout this specification is defined as the ratio of the two components of the adsorbed phase over the ratio of the same two components in the unadsorbed phase at equilibrium conditions. Relative selectivity is shown as Equation 1 below:

Equation 1

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. Equilibrium conditions are determined when the feed mixture passing over a bed of adsorbent does not change composition after contacting the bed of adsorbent or, in other words, when there is no net transfer of material occurring between the unadsorbed and adsorbed phases. Where selectivity of two components approaches 1.0 there is no preferential adsorption of one component by the adsorbent with respect to the other, they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of an extract component of the feed mixture material or, in other words, the relative rate of desorption of an extract component. This characteristic relates directly to the amount of desorbent material that must be employed in the process to recover an extract component from an adsorbent, faster rates of exchange reduce the amount of desorbent material needed to remove an extract component and therefore permit a reduction in the operating cost of the process. With faster rates of exchange, less desorbent material has to be pumped through the process and separated from an extract stream for reuse in the process.

A dynamic testing apparatus is employed to test various adsorbents with particular feed mixtures and desorbent materials to measure the adsorbent characteristics of adsorptive capacitiy, selectivity and exchange rate. The apparatus consists of an adsorbent chamber of approximately 70 cc volume having inlet and outlet portions at opposite ends of the chamber. The chamber is contained with a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantatively or determine qualitatively one or more components in the effluent stream leaving the adsorbent chamber. A pulse test, performed using this apparatus and the following general procedure, is used to determine selectivities and other data for various adsorbent systems. An adsorbent is filled to equilibrium with a particular desorbent material by passing the desorbent material through the adsorbent chamber containing the adsorbent. At a convenient time, a pulse of feed containing known concentrations of a tracer and of a particular extract component or of a raffinate component or both all diluted in desorbent is injected for a duration of several minutes. Desorbent flow is resumed, and the tracer and the extract component or the raffinate component (or both) are eluted as in a liquid-solid chromatographic operation. The effluent can be analyzed onstream or alternatively effluent samples can be collected periodically and later analyzed separately be analytical equipment and traces of the envelopes of corresponding component peaks developed.

From information derived from the test adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, a feed mixture and a desorbent material are being introduced through two of the lines and a raffinate and an extract stream are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Cal., Mar. 28 through Apr. 2, 1971.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network to form cage-like structures. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves" particularly when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of a fatty-acid ester is apparently more dependent on differences in electrochemical attraction of fatty-acid esters and the adsorbent rather than on physical size differences in the fatty-acid-ester molecules.

In hydrated form, the crystalline aluminosilicates generally encompass those zeolites represented by the Formula 1 below:

Formula 1

$$M_{2/n}O:Al_2O_3:wSiO_2:yH_2O$$

where "M" is a cation which balances the electrovalence of the alumin-centered tetrahedra and which is generally referred to as an exchangeable cationic site, "n" represents the valence of the cation, "w" represents the moles of $SiO_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,120,007 respectively incorporated herein by reference thereto. The X zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio of X zeolite is $2.5\pm0.5$. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where "M" is at least one cation having a valence not more than 3, "n" represents the valence of "M", "w" is a value greater than about 3 up to about 6, and "y" is a value up to about 9 depending upon the identity of "M" and the degree of hydration of the crystal. The SiO$_2$/Al$_2$O$_3$ mole ratio for Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well known to those having ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-X or sodium-Y zeolite can be partially or essentially completely replaced with other cations.

The term "base material" as used herein shall refer to a material containing an X or a Y zeolite and amorphous material which can be used to make the adsorbents used in our process. The zeolite will typically be present in the base material in amounts ranging from about 75 wt. % to about 98 wt. % of the base material based on volatile free composition. Volatile free compositions are generally determined after the base material has been calcined at 900° C. in order to drive off all volatile matter. The remainder of the base material will generally be amorphous material such as silica, alumina or silica-alumina mixtures or compounds, such as clays, which material is present in intimate mixture with the small particles of the zeolite material. This amorphous material may be an adjunct of the manufacturing process for X or Y zeolite (for example, intentionally incomplete purification of either zeolite during its manufacture) or it may be added to relatively pure X or Y zeolite but in either case its usual purpose is as a binder to aid in forming or agglomerating the hard crystalline particles of the zeolite. Normally the base material will be in the form of particles such as extrudates, aggregates, tablets, macrospheres or granules having a desired particle size range. The adsorbent used in our process will preferably have a particle size range of about 16–60 mesh (Standard U.S. Mesh). Examples of suitable base materials which can be used to make the adsorbents employed in our process are "Molecular Sieves 13X" and "SK-40" both of which are available from the Linde Company, Tonawanda, N.Y. The first material of course contains X zeolite while the latter material contains Y zeolite.

It is known that X or Y zeolites containing certain cations at the exchangeable cationic sites possess the selectivity requirement and other necessary requirements previously discussed and are therefore suitable for use in this process. Specifically, first adsorbents comprising a X or a Y zeolite containing at exchangeable cationic sites at least one cation selected from the group consisting of cations of metals of Group IA of the Periodic Table of Elements are suitable for use in the first stage of my process to separate an ester of a polyethanoid fatty acid from an ester of a monoethanoid fatty acid and an ester of a saturated fatty acid. Preferably the first adsorbent will comprise a X or a Y zeolite containing sodium or potassium cations at the exchangeable cationic sites. A first adsorbent comprising a X or a Y zeolite containing potassium cations at the exchangeable cationic sites is more preferred than one containing sodium cations at the exchangeable cationic sites because of its higher selectivities. Preferably the X or Y zeolite will be essentially completely exchanged with a selected cation or cations. A non-sodium X or Y zeolite is deemed to be essentially completely exchanged when the residual sodium content of the zeolite after ion exchange is less than about 2 wt. % Na$_2$O. A sodium-X or sodium-Y zeolite is deemed to be essentially completely exchanged when the amount of non-sodium cations occupying exchangeable cationic sites is less than about 2 wt. %. Second adsorbents comprising a X or a Y zeolite containing at exchangeable cationic sites cations selected from the group consisting of pi-bonding metals and one or more second cations selected from the group consisting of sodium, potassium, rubidium and cesium, are suitable for use in the second stage of my process to separate an ester of a monoethanoid fatty acid from an ester of a saturated fatty acid. Copper cations are preferred for the second adsorbent because of the combination of their ability to form complexes with unsaturated-fatty-acid esters and their chemical stability. While other cations such as cations of silver and mercury have the ability to form complexes with unsaturated-fatty-acid esters, in contrast to copper cations they slowly reduce to the elemental metal state. Preferably the X or Y zeolite will be essentially completely exchanged with the selected cations. When the second cation is sodium, the X or Y zeolite is deemed to be essentially completely exchanged when the amount of cations other than copper and sodium occupying exchangeable cationic sites is less than about 2 wt. %. When the second cation is not sodium the X or Y zeolite is deemed to be essentially completely exchanged when the residual sodium content of the zeolite after ion exchange is less than about 2 wt. % Na$_2$O. Preferably the second cation will be potassium and a more preferred second adsorbent will therefore comprise a X or a Y zeolite essentially completely exchanged with copper and potassium cations. More preferably the weight ratio of copper cations to potassium cations in the second adsorbent will be from about 1:1 to about 10:1.

The first and second adsorbents may each be employed in the form of a dense fixed bed which is alternatively contacted with a feed mixture and a desorbent material in which case the process will be only semi-continuous. In another embodiment a set of two or more static beds may be employed for each adsorbent with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. The use of such flow systems is therefore preferred in my process. In a more preferred embodiment my process will employ for each adsorbent a separate simulated moving-bed countercurrent flow system. The operating principles and sequence of operation of one such simulated moving-bed countercurrent flow system are described in U.S. Pat. No. 2,985,589 incorporated herein by reference thereto. In such a system it is the progressive movement of multiple liquid access points down an adsorbent chamber that simulated the upward movement of an adsorbent contained in the chamber. Only four of the access lines are active at any one time; the feed input stream, desorbent inlet stream, raffinate outlet stream, and extract outlet stream access lines. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in each simulated moving-bed countercurrent flow system in order for the desired operations to take place although in some instances an optional fourth zone may be used.

The adsorption zone, zone 1, is defined as the adsorbent located between a feed inlet stream and a raffinate outlet stream. In this zone, a feed mixture contacts an adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between an extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 (hereinafter described) into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between a desorbent inlet stream and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating the extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of an adsorbent than some other operational zone. For instance, in some operations the buffer zone can contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an adsorbent be located in a single column which is divided into zones, and the use of multiple chambers or a series of columns is also within the scope of this embodiment.

It is not necessary that all of the input or output streams be simultaneously used, and in fact, in many instances some of the streams can be shut off while others effect an input or output of material. One apparatus which can be utilized to effect the process of this invention in a preferred embodiment will contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations function intermittently as a conduit through which material passes into or out of the process.

Both extract output streams will pass into a single separation means wherein at least a portion of the desorbent material can be separated to produce a combined extract product containing a reduced concentration of desorbent material. Preferably, but not necessary to the operation of the process, at least a portion of one or both raffinate output streams will also be passed to a separation means wherein at least a portion of a desorbent material can be separated to produce a desorbent stream which can be reused in the process and a raffinate product containing a reduced concentration of desorbent material. The separation means will typically be a fractionation column, the design and operation of which is well known to the separation art.

The use of a single separation means for both extract output streams is made possible by the use of desorbent material having the same composition for both the first and second adsorbents. The advantages of a single separation means lie in a simplicity of operation of the overall process and a reduction in operating expenses and the initial required capital investment.

Reference can be made to D. B. Broughton U.S. Pat. No. 2,985,589 and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 100° C. to about 200° C. being more preferred and a pressure range of from about atmospheric to about 500 psig. with from about atmospheric to about 250 psig. being more preferred to insure liquid phase. Desorption conditions will include the same range of temperatures and pressures as used for adsorption conditions.

The size of the units which can utilize the process of this invention can vary anywhere from those of pilot-plant scale (see for example our assignee's U.S. Pat. No. 3,706,812) to those of commercial scale and can range in flow rates from as little as a few cc an hour up to many thousands of gallons per hour.

The following illustrative embodiment is presented to illustrate the unique flow scheme of my invention and is not intended to unduly restrict the scope and spirit of the claims attached hereto.

ILLUSTRATIVE EMBODIMENT AND DESCRIPTION OF THE DRAWING

The following illustrates my process when operated in a preferred embodiment, i.e. one which utilizes a continuous, simulated moving-bed, countercurrent-flow system in each adsorbent bed with a K-Y zeolite as the first adsorbent and a Cu-K-Y zeolite adsorbent as the second adsorbent. The adsorbents are obtained by essentially complete ion exchanging, by methods well known to those skilled in the art, a portion of Linde 13X Molecular Sieves base material and portion of Linde SK-40 base material with potassium cations, to acquire the K-Y adsorbent, and then a portion of the K-Y adsorbent is exchanged with copper cations, to achieve a Cu to K weight ratio of about 3:1, to acquire the K-Cu-X zeolite adsorbent. The adsorbents have a particle size range of approximately 16-60 U.S. Mesh.

Specifically, this embodiment presents a flow scheme with illustrative details as to operating conditions and stream compositions, for a pilot-plant-scale testing apparatus, one of which is used for each adsorbent, known as a carousel unit, which is described in detail in deRosset et al U.S. Pat. No. 3,706,816 incorporated herein by reference. Briefly, the apparatus consists essentially of 24 serially connected adsorbent chambers having about 18.8 cc. volume each. Total chamber volume of the apparatus is approximately 450 cc. The individual adsorbent chambers are serially connected to each other with relatively small-diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids flow to and from the process. The rotary valve contains a feed input line through which passes a feed mixture containing an extract and a raffinate component, an extract stream outlet line through which passes desorbent material, in admixture with an extract component, a desorbent material inlet line through which passes desorbent material and a raffinate stream outlet line through which passes a raffinate component in admixture with desorbent material. Additionally, a flush material inlet line was used to admit flush material for the purpose of flushing feed components from lines which had previously contained feed material and which were to subsequently contain a raffinate or extract output stream. The flush material employed is desorbent material which leaves the apparatus as part of the extract and raffinate output streams.

The ester feed mixture is a mixture of methyl esters of fatty acids having the composition shown in Table 1:

Table No. 1

| Feed Mixture Composition, Vol. % Methyl Esters of Fatty Acids | |
| --- | --- |
| $C_{14}$ and lower saturated | 1 |
| $C_{16}^0$ saturated (methyl palmitate) | 25 |
| $C_{18}^0$ saturated (methyl stearate) | 18 |
| $C_{18}^1$ = one double bond (methyl oleate) | 45 |
| $C_{18}^2$ = two double bonds (methyl linoleate) | 11 |
| | 100 |

The desorbent material used comprises toluene.

Now, with reference to the drawing, the feed mixture is passed via line 1 to adsorption column 2 which contains the K-Y adsorbent. The operating pressure and temperature for adsorption column 2 is 150 psig. and 60° C., respectively. Substantially all of the methyl linoleate and a portion of the methyl oleate are selectively adsorbed as extract in adsorption column 2. The desorbent material effecting desorption of the extract in adsorption column 2 is introduced thereto via line 9.

The first extract stream leaves adsorption column 2 via line 5 and passes thereby to fractionation 4 for removal of desorbent material. The first extract stream has, on a desorbent material free basis, the composition shown in Table No. 2:

Table No. 2

| First Extract Stream Composition, Vol. % | |
| --- | --- |
| Methyl oleate | 31.3 |
| Methyl linoleate | 68.7 |
| | 100.0 |

The first raffinate stream leaves adsorption column 2 via line 3 and passes thereby to fractionator 6 for removal of a substantial portion of desorbent material therefrom. This first raffinate stream, as well as the first raffinate product from the bottom of fractionator 6, has, on a desorbent material free basis, the composition shown in Table No. 3:

Table No. 3

| First Raffinate Stream Composition, Vol. % | |
| --- | --- |
| $C_{14}$ and lower saturated | 1.2 |
| Methyl palmitate | 29.8 |
| Methyl stearate | 21.4 |
| Methyl oleate | 47.6 |
| | 100.0 |

The first raffinate product stream passes from the bottom of fractionator 6 via line 7 to adsorption column 8 which contains the Cu-K-Y adsorbent. The operating pressure and temperature for adsorption column 8 is 150 psig. and 60° C., respectively. Substantially all of the methyl oleate is selectively adsorbed as extract in adsorption column 8. The desorbent material effecting desorption of the extract in adsorption column 8 is introduced thereto via line 10.

The second extract stream, comprising substantially pure methyl oleate, leaves adsorption column 8 via line 11 and passes thereby to fractionator 4 for removal of desorbent material.

The second raffinate stream leaves adsorption column 8 via line 12 and passes thereby to fractionator 13 for removal of substantially all desorbent material therefrom. The second raffinate stream, as well as the second raffinate product from the bottom of fractionator 13, has, on a desorbent material free basis, the composition shown in Table No. 4:

Table No. 4

| Second Raffinate Stream Composition, Vol. % | |
| --- | --- |
| $C_{14}$ and lower saturated | 2.3 |
| Methyl palmitate | 56.8 |
| Methyl stearate | 40.9 |
| | 100.0 |

The second raffinate product stream passes from the bottom of fractionator 13 as a final process product stream via line 14.

Fractionator 4 is thus the recipient of both the first and second extract streams. A final process product stream, substantially free of desorbent material, passes from the bottom of fractionator 4 via line 15. This stream comprises substantially all of the methyl oleate and methyl linoleate brought into the process as part of the feed mixture.

Desorbent material passes from fractionator 6 to adsorption column 2 via lines 19 and 9, from fractionator 13 to adsorption column 8 via lines 18 and 10, and from fractionator 4 to both adsorption columns via lines 16, 17, 9 and 10.

I claim as my invention:

1. A process for separating an ester of a polyethanoid fatty acid and an ester of a monoethanoid fatty acid from a first mixture comprising an ester of a polyethanoid fatty acid, an ester of a monoethanoid fatty acid and an ester of a saturated fatty acid which process comprises the steps of:

(a) contacting said first mixture at first adsorption conditions with a first adsorbent comprising a X or a Y zeolite containing at the exchangeable cationic sites at least one cation selected from the group consisting of cations of metals of Group IA of the Periodic Table of Elements and combinations thereof thereby selectively adsorbing said ester of a polyethanoid fatty acid;

(b) removing from said first adsorbent a first raffinate output stream comprising said ester of a monoethanoid fatty acid and said ester of a saturated fatty acid;

(c) contacting said first adsorbent at first desorption conditions with a desorbent material to effect the desorption of said ester of a polyethanoid fatty acid from said first adsorbent;

(d) removing from said first adsorbent a first extract output stream comprising said ester of a polyethanoid fatty acid;

(e) contacting a second mixture comprising said first raffinate output stream at second adsorption conditions with a second adsorbent comprising a X or a Y zeolite containing at exchangeable cationic sites cations selected from the group consisting of pi-bonding metals and one or more second cations selected from the group consisting of sodium, potassium, rubidium and cesium, thereby selectively adsorbing said ester of a monoethanoid fatty acid;

(f) removing from said second adsorbent a second raffinate output stream comprising said ester of a saturated fatty acid;

(g) contacting said second adsorbent at second desorption conditions with a desorbent material having the same composition as the desorbent material used in step (c) above to effect the desorption of said ester of a monoethanoid fatty acid from said second adsorbent;

(h) removing from said second adsorbent a second extract output stream comprising said ester of a monoethanoid fatty acid;

(i) passing said first extract output stream and said second extract output stream to a single desorbent recovery means and therein fractionating said output streams in admixture to separate substantially all of said desorbent material from the extracted esters of polyethanoid and monoethanoid fatty acids contained in the admixed output streams;

(j) supplying separate portions of the desorbent material from step (i) to said first and second adsorbents in steps (c) and (g), respectively, to remove adsorbed esters therefrom; and (k) recovering from said desorbent recovery means an extract product stream comprising substantially all of said esters of a polyethanoid fatty acid and monoethanoid fatty acid contained in said first mixture.

2. The process of claim 1 further characterized in that said ester of a polyethanoid fatty acid, said ester of a monoethanoid fatty acid and said ester of a saturated fatty acid each contain from about 8 to about 30 carbon atoms per molecule.

3. The process of claim 2 further characterized in that said ester of a polyethanoid fatty acid, said ester of a monoethanoid fatty acid and said ester of a saturated fatty acid are methyl esters.

4. The process of claim 3 further characterized in that said ester of a polyethanoid fatty acid is methyl linoleate.

5. The process of claim 3 further characterized in that said ester of a monoethanoid fatty acid is methyl oleate.

6. The process of claim 3 further characterized in that said ester of a saturated fatty acid is methyl palmitate or methyl stearate.

7. The process of claim 1 further characterized in that said first adsorbent contains sodium cations at the exchangeable cationic sites.

8. The process of claim 1 further characterized in that said first adsorbent contains potassium cations at the exchangeable cationic sites.

9. The process of claim 1 further characterized in that said second cation of said second adsorbent is potassium and that said second adsorbent is essentially completely exchanged with potassium and copper cations.

10. The process of claim 9 further characterized in that the weight ratio of copper cations to potassium cations is from about 1:1 to about 10:1.

11. The process of claim 1 further characterized in that said first and second adsorption conditions include a temperature within the range of from about 20° C. to about 250° C. and a pressure within the range from about atmospheric to about 500 psig.

12. The process of claim 11 further characterized in that it is effected in the liquid phase.

13. The process of claim 1 further characterized in that said desorbent material comprises a monocyclic aromatic hydrocarbon.

14. The process of claim 13 further characterized in that said monocyclic aromatic hydrocarbon is selected from the group consisting of benzene, toluene, xylenes, ethylbenzene, and diethylbenzenes.

* * * * *